United States Patent
Holton, Jr. et al.

(10) Patent No.: US 11,129,898 B2
(45) Date of Patent: Sep. 28, 2021

(54) NICOTINE-CONTAINING PHARMACEUTICAL COMPOSITION

(71) Applicant: MODORAL BRANDS INC., Winston-Salem, NC (US)

(72) Inventors: Darrell Holton, Jr., Clemmons, NC (US); Nelly Fransén, Helsingborg (SE); Matt Reddick, Clemmons, NC (US)

(73) Assignee: Modoral Brands Inc., Winston-Salem, NC (US)

( * ) Notice: Subject to any disclaimer, the term of this patent is extended or adjusted under 35 U.S.C. 154(b) by 1598 days.

(21) Appl. No.: 14/540,754

(22) Filed: Nov. 13, 2014

(65) Prior Publication Data

US 2015/0071972 A1 Mar. 12, 2015

Related U.S. Application Data

(62) Division of application No. 13/240,500, filed on Sep. 22, 2011, now abandoned.

(51) Int. Cl.

| | |
|---|---|
| A61K 47/26 | (2006.01) |
| A23L 27/10 | (2016.01) |
| A23L 27/20 | (2016.01) |
| A23L 27/30 | (2016.01) |
| A23L 27/40 | (2016.01) |
| A61K 31/465 | (2006.01) |
| A61K 9/00 | (2006.01) |
| A61K 9/70 | (2006.01) |
| A61K 9/20 | (2006.01) |

(52) U.S. Cl.
CPC .............. *A61K 47/26* (2013.01); *A23L 27/10* (2016.08); *A23L 27/2028* (2016.08); *A23L 27/33* (2016.08); *A23L 27/40* (2016.08); *A61K 9/0056* (2013.01); *A61K 9/20* (2013.01); *A61K 9/7007* (2013.01); *A61K 31/465* (2013.01)

(58) Field of Classification Search
CPC ........ A61K 47/26; A61K 9/20; A61K 9/7007; A61K 9/0056; A61K 31/465; A23L 27/40; A23L 27/33; A23L 27/2028; A23L 27/10

See application file for complete search history.

(56) References Cited

U.S. PATENT DOCUMENTS

| | | | |
|---|---|---|---|
| 2,033,909 | A | 3/1936 | Cox et al. |
| 3,114,642 | A | 12/1963 | Meisel |
| 3,341,414 | A | 9/1967 | Cherkas et al. |
| 3,438,787 | A | 4/1969 | Du Ross |
| 3,738,845 | A | 6/1973 | Liebrand |
| 3,901,248 | A | 8/1975 | Lichtneckert et al. |
| 4,144,895 | A | 3/1979 | Fiore |
| 4,150,677 | A | 4/1979 | Osborne, Jr. et al. |
| 4,267,847 | A | 5/1981 | Reid |
| 4,289,147 | A | 9/1981 | Wildman et al. |
| 4,351,346 | A | 9/1982 | Brummer et al. |
| 4,359,059 | A | 11/1982 | Brummer et al. |
| 4,452,825 | A | 6/1984 | Klacik et al. |
| 4,506,682 | A | 3/1985 | Muller |
| 4,589,428 | A | 5/1986 | Keritsis |
| 4,605,016 | A | 8/1986 | Soga et al. |
| 4,716,911 | A | 1/1988 | Poulose et al. |
| 4,727,889 | A | 3/1988 | Niven, Jr. et al. |
| 4,806,356 | A | 2/1989 | Shaw |
| 4,887,618 | A | 12/1989 | Bernasek et al. |
| 4,941,484 | A | 7/1990 | Clapp et al. |
| 4,967,771 | A | 11/1990 | Fagg et al. |
| 4,967,773 | A | 11/1990 | Shaw |
| 4,986,286 | A | 1/1991 | Roberts et al. |
| 5,005,593 | A | 4/1991 | Fagg |
| 5,018,540 | A | 5/1991 | Grubbs et al. |
| 5,060,669 | A | 10/1991 | White et al. |
| 5,065,775 | A | 11/1991 | Fagg |
| 5,074,319 | A | 12/1991 | White et al. |
| 5,098,730 | A | 3/1992 | Pepper et al. |
| 5,099,862 | A | 3/1992 | White et al. |
| 5,110,605 | A | 5/1992 | Acharya |
| 5,121,757 | A | 6/1992 | White et al. |
| 5,131,414 | A | 7/1992 | Fagg et al. |
| 5,131,415 | A | 7/1992 | Munoz et al. |
| 5,148,819 | A | 9/1992 | Fagg |
| 5,197,494 | A | 3/1993 | Kramer |
| 5,230,354 | A | 7/1993 | Smith et al. |
| 5,234,008 | A | 8/1993 | Fagg |
| 5,243,999 | A | 9/1993 | Smith |
| 5,301,694 | A | 4/1994 | Raymond et al. |

(Continued)

FOREIGN PATENT DOCUMENTS

| | | |
|---|---|---|
| EP | 1 421 856 | 5/2004 |
| EP | 2 233 134 | 9/2010 |

(Continued)

OTHER PUBLICATIONS

Michaud, "Pharmaceutical Confectionery," Sep. 1, 2002, Downloaded from Internet, http://www.b5srl.com/downloadArticles.php?aut+MICHAUD,%20JACQUES%3Cbr%3E&mode=product&prod_down=1&product_code=0000000263&n=1&default_table=_product_due.

*Primary Examiner* — Hasan S Ahmed

(74) *Attorney, Agent, or Firm* — Womble Bond Dickinson (US) LLP

(57) ABSTRACT

A composition intended to be employed for therapeutic purposes incorporates a nicotinic compound, a sugar substitute, and a sugar alcohol syrup. Representative forms of nicotine include free base (e.g., as a mixture of nicotine and microcrystalline cellulose), a nicotine salt (e.g., as nicotine bitartrate) or nicotine polacrilex. The composition is useful for treatment of central nervous system conditions, diseases, and disorders, and as a nicotine replacement therapy.

24 Claims, No Drawings

(56) References Cited

U.S. PATENT DOCUMENTS

| | | |
|---|---|---|
| 5,314,701 A | 5/1994 | Mentink et al. |
| 5,318,050 A | 6/1994 | Gonzalez-Parra et al. |
| 5,343,879 A | 9/1994 | Teague |
| 5,360,022 A | 11/1994 | Newton et al. |
| 5,362,496 A | 11/1994 | Baker et al. |
| 5,435,325 A | 7/1995 | Clapp et al. |
| 5,445,169 A | 8/1995 | Brinkley et al. |
| 5,512,306 A | 4/1996 | Carlsson et al. |
| 5,525,351 A | 6/1996 | Dam |
| 5,549,906 A | 8/1996 | Santus |
| 5,593,684 A | 1/1997 | Baker et al. |
| 5,629,042 A | 5/1997 | Serpelloni et al. |
| 5,656,284 A | 8/1997 | Balkin |
| 5,711,961 A | 1/1998 | Reiner et al. |
| 5,733,574 A | 3/1998 | Dam |
| 5,811,126 A | 9/1998 | Krishnamurthy |
| 5,840,334 A | 11/1998 | Raiden et al. |
| 5,869,098 A | 2/1999 | Misra et al. |
| 5,939,100 A | 8/1999 | Albrechtsen et al. |
| 6,024,981 A | 2/2000 | Khankari et al. |
| 6,083,531 A | 7/2000 | Humbert-Droz et al. |
| 6,090,401 A | 7/2000 | Gowan, Jr. et al. |
| 6,110,495 A | 8/2000 | Dam |
| 6,131,584 A | 10/2000 | Lauterbach |
| 6,183,775 B1 | 2/2001 | Ventouras |
| 6,221,392 B1 | 4/2001 | Khankari et al. |
| 6,248,760 B1 | 6/2001 | Wilhelmsen |
| 6,264,981 B1 | 7/2001 | Zhang et al. |
| 6,280,761 B1 | 8/2001 | Santus |
| 6,298,859 B1 | 10/2001 | Kierulff et al. |
| 6,426,090 B1 | 7/2002 | Ream et al. |
| 6,569,463 B2 | 5/2003 | Patel et al. |
| 6,583,160 B2 | 6/2003 | Smith et al. |
| 6,585,997 B2 | 7/2003 | Moro et al. |
| 6,586,449 B1 | 7/2003 | Walling |
| 6,676,959 B1 | 1/2004 | Andersson et al. |
| 6,772,767 B2 | 8/2004 | Mua et al. |
| 6,828,336 B2 | 12/2004 | Walling |
| 6,849,286 B1 | 2/2005 | Bayerköhler et al. |
| 6,872,405 B2 | 3/2005 | Takaishi et al. |
| 6,890,559 B1 | 5/2005 | Bayerköhler et al. |
| 6,893,654 B2 | 5/2005 | Pinney et al. |
| 7,025,983 B2 | 4/2006 | Leung et al. |
| 7,122,198 B1 | 10/2006 | Singh et al. |
| 7,163,705 B2 | 1/2007 | Johnson et al. |
| 7,337,782 B2 | 3/2008 | Thompson |
| 7,374,779 B2 | 5/2008 | Chen et al. |
| 8,343,532 B2 | 1/2013 | Dam et al. |
| 8,501,164 B2 | 8/2013 | Chen |
| 8,545,870 B2 | 10/2013 | Dupinay et al. |
| 2001/0016593 A1 | 8/2001 | Wilhelmsen |
| 2002/0009464 A1 | 1/2002 | Colaco |
| 2003/0176467 A1 | 9/2003 | Andersson et al. |
| 2003/0215553 A1 | 11/2003 | Ribadeau-Dumas et al. |
| 2003/0232082 A1 | 12/2003 | Li et al. |
| 2003/0235617 A1 | 12/2003 | Martino et al. |
| 2004/0052851 A1 | 3/2004 | Graff et al. |
| 2004/0076665 A1 | 4/2004 | Graff et al. |
| 2004/0096501 A1 | 5/2004 | Vaya et al. |
| 2004/0101543 A1 | 5/2004 | Liu et al. |
| 2004/0191322 A1 | 9/2004 | Hansson |
| 2004/0253307 A1 | 12/2004 | Hague et al. |
| 2005/0002993 A1 | 1/2005 | Goggin et al. |
| 2005/0053665 A1 | 3/2005 | Ek et al. |
| 2005/0123502 A1 | 6/2005 | Chan et al. |
| 2006/0120974 A1 | 6/2006 | Mcneight |
| 2006/0171969 A1 | 8/2006 | Macelloni |
| 2006/0171994 A1 | 8/2006 | Dupinay et al. |
| 2006/0191548 A1 | 8/2006 | Strickland et al. |
| 2007/0062549 A1 | 3/2007 | Holton, Jr. et al. |
| 2007/0081949 A1 | 4/2007 | Dam et al. |
| 2007/0178123 A1 | 8/2007 | Levenson et al. |
| 2007/0269386 A1 | 11/2007 | Steen et al. |
| 2007/0269492 A1 | 11/2007 | Steen et al. |
| 2008/0020050 A1 | 1/2008 | Chau et al. |
| 2008/0038209 A1 | 2/2008 | Andersen |
| 2008/0173317 A1 | 7/2008 | Robinson et al. |
| 2008/0286340 A1 | 11/2008 | Andersson et al. |
| 2008/0286341 A1 | 11/2008 | Andersson et al. |
| 2009/0004248 A1 | 1/2009 | Bunick et al. |
| 2009/0014018 A1 | 1/2009 | Sengupta et al. |
| 2009/0023819 A1 | 1/2009 | Axelsson |
| 2009/0025738 A1 | 1/2009 | Mua et al. |
| 2009/0081291 A1 | 3/2009 | Gin et al. |
| 2009/0092573 A1 | 4/2009 | Andersen |
| 2009/0098242 A1 | 4/2009 | Nissen |
| 2009/0208602 A1 | 8/2009 | Kowalczyk et al. |
| 2009/0263544 A1 | 10/2009 | Soldani |
| 2009/0293889 A1 | 12/2009 | Kumar et al. |
| 2010/0004294 A1 | 1/2010 | Axelsson et al. |
| 2010/0061940 A1 | 3/2010 | Axelsson et al. |
| 2010/0124560 A1 | 5/2010 | Hugerth et al. |
| 2010/0247586 A1 | 9/2010 | Hugerth et al. |
| 2010/0300463 A1 | 12/2010 | Chen et al. |
| 2011/0139164 A1 | 6/2011 | Mua et al. |
| 2011/0220130 A1 | 9/2011 | Mua et al. |
| 2011/0268809 A1 | 11/2011 | Brinkley et al. |
| 2012/0244104 A1 | 9/2012 | Mehta et al. |

FOREIGN PATENT DOCUMENTS

| | | |
|---|---|---|
| KR | 2010 0117950 | 11/2010 |
| WO | WO 91/06288 | 5/1991 |
| WO | WO 02/076211 | 10/2002 |
| WO | WO 2005/023226 | 3/2005 |
| WO | WO 2006/114604 | 11/2006 |
| WO | WO 2007/104574 | 9/2007 |
| WO | WO 2008/112124 | 9/2008 |
| WO | WO 2008/140371 | 11/2008 |
| WO | WO 2008/140372 | 11/2008 |
| WO | WO 2009/037319 | 3/2009 |
| WO | WO 2010/044736 | 4/2010 |
| WO | WO 2011/139684 | 11/2011 |

NICOTINE-CONTAINING PHARMACEUTICAL COMPOSITION

CROSS-REFERENCE TO RELATED APPLICATIONS

This application is a divisional of U.S. application Ser. No. 13/240,500, filed Sep. 22, 2011, which is incorporated by reference herein in its entirety.

FIELD OF THE INVENTION

The present invention relates to compositions that contain nicotine, and in particular, to nicotine-containing pharmaceutical compositions intended to be administered to provide a pharmacological effect, or otherwise used for therapeutic purposes.

BACKGROUND OF THE INVENTION

Central nervous system (CNS) conditions, diseases, or disorders can be drug induced; can be attributed to genetic predisposition, infection or trauma; or can be of unknown etiology. They comprise neuropsychiatric disorders, neurological diseases and mental illnesses; and include neurodegenerative diseases, behavioral disorders, cognitive disorders and cognitive affective disorders. The clinical manifestations of several CNS conditions, diseases or disorders have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors).

Nicotinic compounds, such as nicotine, are capable of affecting nicotinic acetylcholinergic receptors (nAChRs). Subtypes of nAChRs exist in both the CNS and the peripheral nervous system (PNS), but the distribution of subtypes is heterogeneous. For instance, certain subtypes which are predominant in vertebrate brain, others predominate at the autonomic ganglia, and others predominate at neuromuscular junction. Activation of nAChRs by nicotinic compounds results in neurotransmitter release. See, for example, Dwoskin et al., *Exp. Opin. Ther. Patents*, 10: 1561-1581 (2000); Schmitt et al., *Annual Reports in Med. Chem.* 35: 41-51 (2000); Huang et al., *J. Am. Chem. Soc.*, 127: 14401-14414 (2006); Arneric et al., *Biochem. Pharmacol.*, 74: 1092-1101 (2007) and Millar, *Biochem. Pharmacol.*, 78: 766-776 (2009); which are incorporated herein by reference.

It has been suggested that administration of nicotine, and other nicotinic compounds, can result in various pharmacological effects. See, for example, U.S. Pat. No. 5,583,140 to Bencherif et al.; U.S. Pat. No. 5,723,477 to McDonald et al.; U.S. Pat. No. 7,001,900 to Jacobsen et al.; U.S. Pat. No. 7,135,484 to Dart et al. and U.S. Pat. No. 7,214,686 to Bencherif et al.; and US Pat. Pub. No. 2010/0004451 to Ahmad et al.; which are incorporated herein by reference. As a result, it has been suggested that nicotine, and other nicotinic compounds, can exhibit utility in the treatment of a wide variety of conditions, diseases, and disorders, including those that affect the CNS. Additionally, administration of nicotine and nicotinic compounds has been proposed for treatment of certain other conditions, diseases, and disorders. See, for example, U.S. Pat. No. 5,604,231 to Smith et al.; U.S. Pat. No. 5,811,442 to Bencherif et al.; U.S. Pat. No. 6,238,689 to Rhodes et al.; and U.S. Pat. No. 6,489,349 to Bencherif et al.; which are incorporated herein by reference. Furthermore, administration of nicotine has been employed in an effort to help cigarette smokers quit smoking (i.e., as a smoking cessation aid). For example, nicotine has been an active ingredient of various types of so-called "nicotine replacement therapy" or "NRT" products. See, for example, U.S. patent application Ser. No. 12/769,335 and International Application No. PCT/US2011/033928, both to Brinkley et al., which are incorporated herein by reference.

It has been proposed to administer nicotine using a transdermal patch. Representative types of nicotine-containing transdermal patch products have been marketed under the tradenames "Habitrol," "Nicoderm," "Nicorette," "Nicorette CQ," "Nicotinell" and "Pro Step." See also, for example, U.S. Pat. No. 4,597,961 to Etscom; U.S. Pat. No. 5,298,257 to Bannon et al.; U.S. Pat. No. 5,603,947 to Wong et al.; U.S. Pat. No. 5,834,011 to Rose et al.; U.S. Pat. No. 6,165,497 to Osborne et al, and U.S. Pat. No. 6,676,959 to Anderson et al., which are incorporated herein by reference. It also has been suggested that transdermal administration of nicotine can be accompanied by ingestion of other types of nicotine-containing products. See, for example, U.S. Pat. No. 5,593,684 to Baker et al.; US Pat. Pub. No. 2009/0004249 to Gonda; and Fagerstrom, *Health Values,* 18:15 (1994), which are incorporated herein by reference.

One particularly popular way to provide for oral administration of nicotine has been through the use of nicotine-containing gum. Nicotine-containing gum products have been marketed under the tradenames "Nicorette," "Nicotinell" and "Zonnic." See also, for example, U.S. Pat. No. 3,845,217 to Ferno et al.; U.S. Pat. No. 3,877,468 to Lichtneckert et al.; U.S. Pat. No. 3,901,248 to Lichtneckert et al.; U.S. Pat. No. 6,344,222 to Cherukuri et al.; U.S. Pat. No. 6,358,060 to Pinney et al.; U.S. Pat. No. 6,773,716 to Ream et al. and U.S. Pat. No. 6,893,654 to Pinney et al.; and US Pat. Pub. No. 2004/0191322 to Hansson, which are incorporated herein by reference.

Another way that has been employed to provide oral administration of nicotine has been through the use of nicotine-containing lozenge or tablet types of products. Nicotine-containing lozenge, mini lozenge, tablet, and microtab types of products have been marketed under the tradenames "Commit," "Nicorette," "Nicotinell" and "NiQuitin." See also, for example, U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al. and U.S. Pat. No. 6,248,760 to Wilhelmsen; US Pat. Pub. Nos. 2001/0016593 to Wilhelmsen and 2010/0004294 to Axelsson et al., which are incorporated herein by reference.

Nicotine also has been administered in the form of nasal or oral sprays. Various exemplary ways to administer nicotine in the form of a nasal spray are set forth in U.S. Pat. No. 4,579,858 to Ferno et al.; U.S. Pat. No. 5,656,255 to Jones and U.S. Pat. No. 6,596,740 to Jones, which are incorporated herein by reference. Various exemplary ways to administer nicotine in the form of an oral spray, such as for buccal administration, are set forth in U.S. Pat. No. 6,024,097 to Von Wielligh; US Pat. Pub. Nos. 2003/0159702 to Lindell et al.; 2007/0163610 to Lindell et al. and 2009/0023819 to Axelsson; EP 1458388 to Lindell et al.; and PCT WO 2008/037470 to Axelsson et al., which are incorporated herein by reference. Nicotine-containing sprays have been marketed under the tradenames "Nicotrol NS," "Quit" and "Zonnic."

Various other ways to administer nicotine for the purpose of providing a therapeutic effect have been proposed. For example, it has been suggested that nicotine can be incorporated into orally dissolving films (e.g., U.S. Pat. No.

6,709,671 to Zerbe et al.; U.S. Pat. No. 7,025,983 to Leung et al.; and U.S. Pat. No. 7,491,406 to Leung et al.; and US Pat. Pub. Nos. 2006/0198873 to Chan et al. and 2006/0204559 to Bess et al.); oral osmotic devices (e.g., U.S. Pat. No. 5,147,654 to Place et al.); gum pads (e.g., U.S. Pat. No. 6,319,510 to Yates); oral patches (e.g., US Pat. Pub. No. 2006/0240087 to Houze et al.); snuff-type forms in pouches or sachets (e.g., U.S. Pat. No. 4,907,605 to Ray et al. and US Pat. Pub, No. 2009/0293895 to Axelsson et al.); lip balm (e.g., U.S. Pat. No. 7,105,173 to Rolling) and beverages (e.g., U.S. Pat. No. 6,268,386 to Thompson; U.S. Pat. No. 7,115,297 to Stillman and U.S. Pat. No. 7,435,749 to Knight). It also has been suggested that nicotine can be delivered using various types of inhalation devices and vapor delivery systems (e.g., U.S. Pat. No. 4,284,809 to Ray; U.S. Pat. No. 4,800,903 to Ray et al.; U.S. Pat. No. 6,234,169 to Bulbrook et al. and U.S. Pat. No. 6,874,507 to Farr; and US Pat. Pub. Nos, 2006/0018840 to Lechuga-Ballesteros and 2009/0005423 to Gonda; and EP 1,618,803 to Hon).

It would be desirable to provide alternative compositions capable of delivering or administering nicotine via an oral route for therapeutic purposes.

SUMMARY OF THE INVENTION

In one aspect, the present invention relates to a nicotine-containing composition intended to be employed for therapeutic purposes. The composition is typically in a pharmaceutically acceptable form adapted for oral delivery of the composition. The composition incorporates at least one nicotinic compound, a sugar substitute, and a sugar alcohol syrup. In certain embodiments, the composition exhibits some level of translucency.

In certain embodiments, the present invention provides a nicotine-containing pharmaceutical composition, comprising: a nicotinic compound; at least about 80% by weight of a sugar substitute; and a sugar alcohol syrup, wherein the sugar substitute is a non-hygroscopic sugar alcohol capable of forming a glassy matrix and wherein the composition is in a pharmaceutically acceptable form adapted for oral delivery of the composition. At least a portion of the nicotinic compound can, in certain embodiments, be in the form of a free base, a salt, a complex, or a solvate. For example, the nicotinic compound may comprise nicotine polacrilex. In some embodiments, the nicotinic compound is sorbed onto a porous particulate carrier. For example, the porous particulate carrier can comprise microcrystalline cellulose.

In some embodiments, the sugar substitute is isomalt. In certain embodiments, the sugar alcohol syrup is maltitol syrup or xylitol syrup. The amount of the components can vary. For example, in some embodiments, the composition comprises at least about 85% by weight of the sugar substitute. In some embodiments, the amount of sugar alcohol syrup is that amount sufficient to slow recrystallization of the sugar substitute in melted form. For example, in some embodiments, the composition comprises at least about 4.0% by weight or at least about 4.5% by weight of the sugar alcohol syrup.

Various components can be included within the pharmaceutical composition. For example, in some embodiments, the composition further comprises one or more of flavorants, sweeteners, and NaCl. The amount and type of these components can vary. For example, in some embodiments, the amount of flavorant is from about 0.1 to about 0.5 percent by weight of the pharmaceutical composition. In some embodiments, the flavorant is vanillin and/or mint flavor. In some embodiments, the sweetener comprises sucralose. The amount of NaCl, where included, may be from about 0.5 to about 1 percent by weight of the composition in certain embodiments.

The pharmaceutical composition may take any form. For example, in some embodiments, the composition is in the form of a lozenge or tablet. In certain embodiments, the composition is translucent. In certain embodiments, the composition is transparent.

In another aspect of the invention is provided a method for treating a human subject having a condition, disease, or disorder responsive to stimulation of nicotinic acetylcholinergic receptors, comprising orally administering an effective amount of a pharmaceutical composition according to any of the embodiments noted herein to a human subject (e.g., administering a nicotine-containing pharmaceutical composition, comprising: a nicotinic compound; at least about 80% by weight of a sugar substitute; and a sugar alcohol syrup, wherein the sugar substitute is a non-hygroscopic sugar alcohol capable of forming a glassy matrix and wherein the composition is in a pharmaceutically acceptable form adapted for oral delivery of the composition). For example, the method may involve administering a composition that incorporates a nicotinic compound, a sugar substitute, and a sugar alcohol syrup. The administering step can, in certain embodiments, comprise administering the pharmaceutical composition to a human subject having a condition, disease, or disorder of the central nervous system. The administering step can, in certain embodiments, comprise administering the pharmaceutical composition to a human subject as a smoking cessation aid.

In a further aspect, the invention provides a method of preparing a nicotine-containing pharmaceutical composition, comprising mixing a non-hygroscopic sugar substitute capable of forming a glassy matrix in an amount of at least about 80% by weight and a sugar alcohol syrup, in a melted state to form a mixture; cooling the mixture and incorporating a nicotinic compound into the cooled mixture; and further cooling the mixture to room temperature to form a solid nicotine-containing pharmaceutical composition. Various other steps can be included within this method. For example, the method may, in certain embodiments, further comprise adding one or more components selected from the group consisting of flavorants, sweeteners, and NaCl.

In some embodiments, the mixing step comprises heating the sugar substitute and the sugar alcohol syrup to a temperature above the hard crack stage of the sugar substitute and the incorporating step comprises adding a nicotinic compound to the mixture at a temperature below the hard crack stage of the sugar substitute. For example, in certain specific embodiments, the hard crack stage is about 145° C. to about 155° C. and the sugar substitute and the sugar alcohol syrup are heated at a temperature between the hard crack stage and about 171° C.

DETAILED DESCRIPTION OF THE PREFERRED EMBODIMENTS

The present inventions now will be described more fully hereinafter. The invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The present invention involves the use of nicotinic compounds for therapeutic purposes and provides compositions adapted for oral delivery of nicotinic compounds. As used herein, "nicotinic compound" refers to naturally occurring or synthetic nicotine unbound from a plant material, meaning the compound is at least partially purified and not contained within a plant structure such as a tobacco leaf. Most preferably, nicotine is naturally-occurring and obtained as an extract from a *Nicotiana* species (e.g., tobacco). Exemplary types of tobacco and manners of processing the tobacco are set forth in U.S. patent application Ser. No. 13/095,277 to Byrd et al., which is incorporated herein by reference.

The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis. Despite the fact that nicotine can be extracted from *Nicotiana* species, it is highly preferred that the nicotine (and the composition and products produced in accordance with the present invention) is virtually or essentially absent of other components of tobacco.

In embodiments wherein nicotine is derived from a plant of the *Nicotiana* species, the plant or portions thereof can be subjected to various types of processing conditions to provide the nicotine. For example, components can be separated from one another, or otherwise fractionated into chemical classes or mixtures of individual compounds. Typical separation processes can include one or more process steps (e.g., solvent extraction using polar solvents, organic solvents, or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated herein by reference. In addition, the plant or portions thereof can be subjected to the types of treatments set forth in Ishikawa et al., *Chem, Pharm, Bull.*, 50, 501-507 (2002); Tienpont et al., *Anal. Bioanal. Chem.*, 373, 46-55 (2002); Ochiai, *Gerstel Solutions Worldwide*, 6, 17-19 (2006); Coleman, III, et al., *J. Sci. Food and Agric.*, 84, 1223-1228 (2004); Coleman, III et al., *J. Sci. Food and Agric.*, 85, 2645-2654 (2005); Pawliszyn, ed., *Applications of Solid Phase Microextraction, RSC Chromatography Monographs*, (Royal Society of Chemistry, UK) (1999); Sahraoui et al., *J. Chrom.*, 1210, 229-233 (2008); and U.S. Pat. No. 5,301,694 to Raymond et al., which are all incorporated herein by reference.

In certain embodiments, isolation of nicotine from a plant of the *Nicotiana* species comprises a step of removing high molecular weight components from a tobacco extract. In certain embodiments, high molecular weight components that are beneficially removed according to the present invention include, but are not limited to, high molecular weight Maillard browning polymers, proteins, polysaccharides, certain pigments, and bacteria. Various methods can be used for this purpose, including size exclusion chromatography, microfiltration, ultrafiltration, nanofiltration, reverse osmosis, and combinations thereof.

In one embodiment, ultrafiltration is used to remove high molecular weight components from tobacco material. The ultrafiltration method is typically applied to a tobacco material in the form of a tobacco extract (e.g., an aqueous tobacco extract). In ultrafiltration, the material to be filtered is brought into contact with a semipermeable membrane, The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of any material. For example, polysulfone, polyethersulfone, polypropylene, polyvinylidenefluoride, and cellulose acetate membranes are commonly used, although other materials can be used without departing from the invention described herein.

Ultrafiltration membranes are available in a wide range of pore sizes (typically ranging from about 0.1 to about 0.001 microns). Membranes are more typically described by their number average molecular weight cutoffs. Ultrafiltration membranes are commonly classified as membranes with molecular weight cutoffs of from about $10^3$ Da to about $10^5$ Da. In practice, compounds with molecular weights above the molecular weight cutoff are retained in the retentate, and the compounds with molecular weights below the cutoff pass through the filter into the permeate. Ultrafiltration methods typically are not capable of removing low molecular weight organic compounds and ions.

Ultrafiltration is typically a cross-flow separation process. The liquid stream to be treated (feed) flows tangentially along the membrane surface, separating into one stream that passes through the membrane (permeate) and another that does not (retentate or concentrate). The operating parameters of the ultrafiltration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial ultrafiltration systems are readily available and may be used for the ultrafiltration methods of the present invention. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate™ Centrasette™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and MiniKros® Tangential Flow Filtration Systems.

Filters and/or membranes that may be useful according to the present invention include those with molecular weight cutoffs of less than about 100,000 Da, less than about 75,000 Da, less than about 50,000, less than about 25,000 Da, less than about 20,000 Da, less than about 15,000 Da, less than about 10,000 Da, and less than about 5,000 Da. In certain embodiments, a multistage filtration process is used to provide an extract with improved clarity. Such embodiments employ multiple filters and/or membranes of different (typically decreasing) molecular weight cutoffs. Any number of filters and/or membranes can be used in succession according to the invention. For example, a first filtration may be conducted using a 50,000 Da molecular weight cutoff filter and a second filtration may be conducted using a 5,000 Da molecular weight cutoff filter. Accordingly, the ultrafiltered extract can comprise only compounds with molecular weights below about 50,000, below about 25,000, below about 10,000 Da, below about 7,500 Da, below about 5,000 Da, below about 2,500 Da, or below about 1,000 Da. The ultrafiltered extract typically comprises primarily sugars, nicotine, and amino acids. Ultrafiltration can be used in combination with other separation and purification methods to provide nicotine having an acceptable purity level.

The ultrafiltered extract exhibits a level of improvement in clarity over the non-ultrafiltered extract. Clarity of the extract (and pharmaceutical compositions according to the invention made therefrom), is typically defined in terms of translucency. As used herein, "translucent" or "translucency" refers to materials allowing some level of light to travel therethrough diffusely. In certain embodiments, certain materials of the invention (e.g., certain tobacco extracts or pharmaceutical compositions made therefrom) can have such a high degree of clarity that the material can be classified as "transparent" or exhibiting "transparency," which is defined as a material allowing light to pass freely through without significant diffusion. The clarity of the ultrafiltered extract is such that there is some level of translucency as opposed to opacity (which refers to materials that are impenetrable by light).

The improvement in clarity of the ultrafiltered extract over the non-ultrafiltered extract can be quantified by any known method. For example, optical methods such as turbidimetry (or nephelometry) and colorimetry may be used to quantify the cloudiness (light scattering) and the color (light absorption), respectively, of the ultrafiltered extract or products made therefrom. Translucency can also be confirmed by visual inspection by simply holding the material (e.g., extract) or product up to a light source and determining if light travels through the material or product in a diffuse manner.

In certain embodiments, the ultrafiltered extract is analyzed by contacting the extract with light and measuring the percent of light that has not been absorbed and/or dispersed by the extract. The measurement can be done, for example, using a standard spectrophotometer at a given wavelength. The spectrophotometer is typically calibrated with deionized water, which is assigned a transparency value of 100%. Acceptable levels of translucency/transparency at a given wavelength in the ultrafiltered extract can vary. Typically, the ultrafiltered extract has a translucency of greater than about 5%, greater than about 10%, greater than about 15%, greater than about 20%, greater than about 25%, greater than about 30%, greater than about 40%, greater than about 50%, greater than about 60%, greater than about 60%, greater than about 70%, greater than about 80%, or greater than about 90%. Typically, the ultrafiltered extract will not be colorless, and will have some discernible brown/black coloring. Following ultrafiltration, the extract can be stored in the refrigerator or freezer or the extract can be freeze dried or spray dried prior to further processing to isolate the nicotine therefrom for use in pharmaceutical compositions according to the present invention.

Nicotinic compounds of the invention can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12, 43-54 (1983). Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid as discussed in U.S. patent application Ser. No. 12/769,335 and International Application No. PCT/US2011/033928, both to Brinkley et al., which are incorporated herein by reference.

In one embodiment, the nicotinic compound is sorbed onto a porous particulate carrier material, such as microcrystalline cellulose (MCC) prior to incorporation within the compositions of the invention. In one embodiment, the MCC materials used in the invention have an average particle size range of about 15 to about 250 microns. Exemplary MCC materials include various grades of AVICEL® and VIVACEL® materials. See, for example, US Pat. Pub. No, 2004/0191322 to Hansson, which is incorporated by reference herein. In certain embodiments, multiple forms of nicotinic compounds could be sorbed onto the particulate carrier, including any of the various nicotinic compound combinations discussed herein. In some embodiments, the nicotinic compound and, optionally, an organic acid moiety can be sorbed onto the particulate carrier by, for example, dissolving the nicotinic compound (and, optionally, an organic acid moiety) in a hydrophilic solvent (such as water, alcohol, or mixtures thereof) and combining the solution with the particulate carrier, followed by drying to remove the solvent. The particulate carrier material with the sorbed nicotine and, optionally, organic acid moiety, can be combined with other carriers or excipients in order to provide a composition adapted for oral delivery of the active ingredient.

The compositions of the invention possess a form that is pharmaceutically effective and pharmaceutically acceptable. That is, the composition most preferably does not incorporate to any appreciable degree, or does not purposefully incorporate, components of tobacco, other than nicotine. As such, pharmaceutically effective and pharmaceutically acceptable compositions do not include tobacco, processed tobacco components, or many of the components of tobacco traditionally present within tobacco-containing cigarettes, cigars, pipes, or smokeless forms of tobacco products. Highly preferred compositions include less than 0.5 weight percent of tobacco components other than nicotine, more often less than about 0.25 weight percent, and typically are entirely absent or devoid of components of tobacco, processed tobacco components, or components derived from tobacco, other than nicotine.

The pharmaceutical compositions of the invention may be conveniently made available in a unit dosage form, whereby such formulations may be prepared by any of the methods generally known in the pharmaceutical arts. Generally speaking, such methods of preparation comprise combining (by various methods) an active agent with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

The nicotine-containing pharmaceutical compositions of the invention can incorporate various pharmaceutically acceptable excipients. By "pharmaceutically acceptable carrier" or "pharmaceutically acceptable excipient" is intended a carrier or excipient that is conventionally used in the art to facilitate the storage, administration, and/or the healing effect of an active agent (e.g., a nicotinic compound). The carrier(s) must be pharmaceutically acceptable in the sense of being compatible with the other ingredients of the formulation and not unduly deleterious to the recipient thereof. A carrier may also reduce any undesirable side effects of the agent. See, Wang et al. (1980) *J. Parent. Drug Assn.* 34(6):452-462, herein incorporated by reference in its entirety. Other exemplary pharmaceutical excipients and/or additives suitable for use in the compositions according to the invention are listed in Remington: The Science & Practice of Pharmacy, 21$^{st}$ ed., Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

The various excipients can vary, and the selection and amount of each excipient can depend upon factors such as the ultimate form and function of product that is desired. See, for example, the types of ingredients, relative amounts and combinations of ingredients, nicotine-containing formulations and preparation processes for nicotine-containing products set forth in U.S. Pat. No. 5,512,306 to Carlsson et al.; U.S. Pat. No. 5,525,351 to Dam; U.S. Pat. No. 5,549,906 to Santus; U.S. Pat. No. 5,711,961 to Reiner et al.; U.S. Pat. No. 5,811,126 to Krishnamurthy; U.S. Pat. No. 5,939,100 to Albrechtsen et al.; U.S. Pat. No. 6,024,981 to Khankari et al.; U.S. Pat. No. 6,083,531 to Humbert-Droz et al.; U.S. Pat. No. 6,090,401 to Gowan, Jr. et al.; U.S. Pat. No. 6,110,495 to Dam; U.S. Pat. No. 6,248,760 to Wilhelmsen; U.S. Pat. No. 6,280,761 to Santus; U.S. Pat. No. 6,426,090 to Ream et al.; U.S. Pat. No. 6,569,463 to Patel et al.; U.S. Pat. No. 6,583,160 to Smith et al.; U.S. Pat. No. 6,585,997 to Moro et al.; U.S. Pat. No. 6,676,959 to Andersson et al.; U.S. Pat. No. 6,893,654 to Pinney et al.; U.S. Pat. No. 7,025,983 to Leung et al.; and U.S. Pat. No. 7,163,705 Johnson et al.; US Pat. Pub. Nos. 2003/0176467 to Andersson et al.; 2003/0235617 to Martino et al.; 2004/0096501 to Vaya et al.; 2004/0101543 to Liu et al.; 2004/0191322 to Hansson; 2005/0053665 to Ek et al.; 2005/0123502 to Chan et al.; 2008/0038209 to Andersen et al.; 2008/0286341 to Andersson et al.; 2009/0023819 to Axelsson; 2009/0092573 to Andersen; 2010/0004294 to Axelsson et al.; and 2010/0061940 to Axelsson et al.; which are incorporated herein by reference.

Although sucrose can be used in the preparation of the nicotine-containing products of the present invention, the products are typically sugar-free products, comprising one or more sugar substitutes. "Sugar-free" as used herein is intended to include products having less than about ⅕th sugar by weight, or less than about ⅒th sugar by weight.

In certain embodiments, the base of the nicotine products described herein is a sugar substitute. By "base" is meant a substance that makes up a relatively high percentage of the nicotine product. The amount of sugar substitute in the nicotine-containing product mixture can vary, but is typically at least about 60%, at least about 75%, at least about 80%, at least about 85%, or at least about 90% by weight of the mixture.

The sugar substitute is typically provided in pure, solid form (e.g., granular or powdered form). In certain embodiments, the sugar substitute is dry, comprising a very low water content. For example, the sugar substitute can comprise less than about 5% water by weight, less than about 3% water by weight, less than about 2% water by weight, or less than about 1% water by weight.

The sugar substitute can be any sugarless material (i.e., sucrose-free material) and can be natural or synthetically produced. The sugar substitute used in the invention can be nutritive or non-nutritive. For example, the sugar substitute is commonly a sugar alcohol. Sugar alcohols that may be useful according to the present invention include, but are not limited to, erythritol, threitol, arabitol, xylitol, ribotol, mannitol, sorbitol, dulcitol, iditol, isomalt, maltitol, lactitol, polyglycitol, and mixtures thereof. For example, in certain embodiments, the sugar alcohol is selected from the group consisting of erythritol, sorbitol, and isomalt.

In certain embodiments, the sugar substitute is capable of forming a glassy matrix, The formation of a glassy matrix is commonly characterized by a translucent/transparent appearance. Typically, the sugar substitute is substantially non-hygroscopic. Non-hygroscopic materials typically do not absorb, adsorb, and/or retain a significant quantity of moisture from the air. For example, in some embodiments, the sugar substitute exhibits a weight gain of water of less than about 50% upon exposure to conditions of 25° C., 80% relative humidity for two weeks. Typically, the sugar substitute exhibits a weight gain of less than about 30%, less than about 20%, less than about 10%, less than about 5%, less than about 2%, or less than about 1% upon exposure to conditions of 25° C., 80% relative humidity for two weeks. Non-hygroscopic materials can provide the benefit of reducing the tendency of the nicotine-containing product to tackify upon exposure to humidity.

In certain embodiments, the sugar substitute comprises one or more sugar alcohols. For example, in one embodiment, the sugar substitute is isomalt. Isomalt is a disaccharide that is typically made by enzymatic rearrangement of sucrose into isomaltulose, followed by hydrogenation to give an equimolar composition of 6-O-α-D-glucopyranosido-D-sorbitol (1,6-GPS) and 1-O-α-D-glucopyranosido-D-mannitol-dihydrate (1,1-GPM-dihydrate).

In addition to the nicotinic compound and sugar substitute, the nicotine-containing product of the present invention typically contains a syrup, e.g., a sugar syrup or a sugar alcohol syrup. "Sugar alcohol syrup" as used herein is intended to refer to a thick solution of sugar alcohol in water, e.g., having greater than about 40% solids, preferably having greater than about 50% solids, greater than about 60% solids, greater than about 70% solids, or greater than about 80% solids, by weight. Typically, the solid content of the sugar alcohol syrup primarily comprises the named sugar alcohol (i.e., maltitol syrup typically comprises greater than about 80%, greater than about 85%, or greater than about 90% by weight maltitol on a dry basis). Sugar alcohol syrups are generally prepared by heating a solution of the sugar alcohol in water and cooling the mixture to give a viscous composition. The resulting syrup is typically characterized by a relatively high concentration of sugar alcohol and relatively high stability (i.e., the sugar alcohol typically does not crystallize from solution, e.g., at room temperature).

The syrup, e.g., sugar alcohol syrup, desirably is capable of affecting the re-crystallization of a melted sugar substitute. One exemplary sugar alcohol syrup that is particularly useful according to the present invention is maltitol syrup. Other sugar alcohol syrups can be used, including, but not limited to, syrups containing xylitol, mannitol, glycerol, erythritol, threitol, arabitol, ribitol, mannitol, sorbitol, dulcitol, iditol, isomalt, lactitol, or polyglycitol. Such sugar alcohol syrups can be prepared or can be obtained from commercial sources. For example, maltitol syrups are commercially available from such suppliers as Corn Products Specialty Ingredients of Newark, Del. Although sugar alcohol syrups may be preferred, sugar syrups can, in certain embodiments, be used in place of or in combination with the sugar alcohol syrup. For example, in some embodiments, corn syrup, golden syrup, and/or molasses can be used.

The amount of sugar alcohol syrup added to the product mixture is typically that amount required to slow recrystallization of the sugar substitute in melted form. One of skill in the art would understand the need to vary the amount of sugar alcohol syrup depending on the composition of the remaining ingredients to ensure that the recrystallization is sufficiently slow to provide a material with the desired characteristics (e.g., a desired level of translucency/transparency). Accordingly, the amount of sugar alcohol syrup can vary, but typically ranges from about 0.1% to about 2%, often from about 0.5% to about 1.5%, and more often about 1% by weight of the nicotine-containing product mixture. In certain embodiments, the amount of sugar alcohol syrup is higher, for example, up to about 2% by weight of the mixture, up to about 5% by weight of the mixture, up to about 10% by weight of the mixture, or up to about 20% by weight of the mixture.

Other pharmaceutically acceptable components may be added to the products of the invention. For example, in certain embodiments, the nicotine-containing pharmaceutical composition further comprises a salt. The presence of a salt in the composition may act to suppress bitterness and/or enhance sweetness. Any type of salt can be used. Common table salt (NaCl) is typically used according to the present invention, but other types of salts are intended to be encompassed as well. The amount of salt added may vary, but typically ranges from 0% to about 8%, for example from about 1% to about 4% or from about 0% to about 2%, often around 1% by weight of the pharmaceutical composition mixture. In some embodiments, a somewhat salty taste is a desirable feature of the pharmaceutical composition.

In some embodiments, the composition according to the invention further comprises one or more buffering agents and/or pH adjusters (e.g., acids or bases). Certain exemplary buffering agents and/or pH adjusters include, but are not limited to, magnesium oxide, magnesium hydroxide, potassium carbonate, sodium carbonate, potassium bicarbonate, sodium bicarbonate, or mixtures thereof. In some embodiments, one or more buffering agents and/or pH adjusters are added to the mixture to ensure that the final pharmaceutical composition has a pH within a desirable range. Exemplary pH ranges in such compositions are generally from about 6-11, and often about 7-10 (e.g., about 7 or about 8). In such embodiments, the amount of buffering agent and/or pH adjuster added to the composition mixture is simply that amount required to bring the formulation to, or keep the formulation at, the desired pH. The amount of buffering agent and/or pH adjuster added to any given formulation can be readily calculated by one skilled in the art and may comprise, for example, about 0.5% to about 1% by weight of the mixture. It is noted that in certain embodiments, a basic pH is not necessary in the products of the present invention. Accordingly, certain products of the present invention have a pH of less than about 6 or less than about 5 (e.g., from about 4 to about 6).

Various food-grade buffering agents are known and can be used to adjust the pH of the products of the present invention. Suitable buffering agents include those selected from the group consisting of acetates, glycinates, phosphates, glycerophosphates, citrates such as citrates of alkaline metals, carbonates, hydrogen carbonates, and borates, and mixtures thereof. In certain embodiments, the buffering agent is an amino acid, as taught for example, in US Pat. Pub. No. 2008/0286341 to Andersson et al. and PCT Appl. No. WO2008/040371 to Andersson et al., which are both incorporated herein by reference. As noted therein, various amino acids and salts thereof are useful for this purpose, including, but not limited to, arginine, asparigine, glutamic acid, glutamine, glycine, histidine, isoleucine, leucine, lysine, methionine, phenylalanine, serine, threonine, valine, cysteic acid, N-glycylglycine, and ornithine. In certain embodiments, N-glycylglycine or L-lysine is added as a buffering agent. In some embodiments, an amino acid buffering agent is used in combination with another amino acid buffering agent and/or in combination with one or more non-amino acid buffering agents. In certain embodiments, the optional pH adjusting agent is a base (e.g., NaOH). In certain embodiments, L-lysine and NaOH are added to the compositions of the present invention.

In some embodiments, one or more additional sweeteners are added to the compositions of the present invention. The one or more additional sweeteners can comprise any natural or artificial sweetener, including, but not limited to, sugar or any of the sugar substitutes described previously. In certain embodiments, the sweetener can include, glycyrrhizin, glycerol, inulin, lactitol, lactose, mabinlin, maltitol, mannitol, miraculin, monatin, monellin, osladin, pentadin, polydextrose, sorbitol, stevia, tagatose, thaumatin, acesulfame potassium, alitame, aspartame, cyclamate, dulcin, glucin, neotame, saccharin, sorbitol, sucralose, xylitol, and combinations thereof. In certain embodiments, the sweetener comprises sucralose (1,6-Dichloro-1,6-dideoxy-β-D-fructofuranosyl-4-chloro-4-deoxy-α-D-galactopyranoside). The amount of sweetener added can vary, but is typically that amount required for a sufficiently "sweet" taste. For example, sweetener can be added to make the sweetness of the nicotine-containing pharmaceutical composition comparable to that of sugar. In particular embodiments, sucralose is added in an amount of about 0.5% to about 2% by weight of the product mixture, often in an amount of about 1% by weight of the mixture.

Various natural and/or artificial flavorants can also be added to the pharmaceutical compositions of the present invention, and the character of these flavors can be described as, without limitation, fresh, sweet, herbal, confectionary, floral, fruity or spicy. Specific types of flavors include, but are not limited to, vanilla (e.g., vanillin optionally in complexed form), coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, and fruit flavors such as lemon, orange, apple, peach, lime, cherry, and strawberry. See also, Leffingwill et al., Tobacco Flavoring for Smoking Products, R. J. Reynolds Tobacco Company (1972), which is incorporated herein by reference. Flavorings also can include components that are considered moistening, cooling or smoothening agents, such as eucalyptus. Flavorings can also include sensates, which can add a range of tactile, organoleptic properties to the pharmaceutical compositions. For example, sensates can provide a warming, cooling, or tingling sensation. These flavors may be provided neat (i.e., alone) or in a composite (e.g., spearmint and menthol, or orange and cinnamon). Flavorants of this type can be present in an amount of from about 0.5% to about 15%, often between about 0.5% and about 1.5% by weight of the mixture. In certain embodiments, the flavorant is present in any amount of at least about 0.5% by weight or at least about 0.75% by weight of the mixture.

It is well-known that nicotine is subject to oxidation and accordingly, it may be advantageous to incorporate one or more anti-oxidants, such as, e.g., ascorbyl palmitate and/or sodium ascorbate, in a composition according to the invention. The one or more anti-oxidants may be present in a concentration of from about 0.05% to about 0.3% by weight, such as, e.g., from about 0.1% to about 0.25% or from about 0.15% to about 0.2% in the pharmaceutical composition mixture.

Various other substances can be added to the compositions of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No, 10), and lubricants or processing aids (e.g, calcium stearate or magnesium stearate) are added to the compositions in certain embodiments.

Certain types of nicotine-containing products also can have outer coatings composed of ingredients capable of providing acceptable outer coatings (e.g., an outer coating can be composed of ingredients such as carnauba wax, and pharmaceutically acceptable forms of shellacs, glazing compositions and surface polish agents). Application of a coating can be accomplished using techniques such as airless spraying, fluidized bed coating, use of a coating pan, or the like. Materials for use as a coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Formulations of the present invention may include short-term, rapid-onset, rapid-offset, controlled release, sustained release, delayed release, and pulsatile release formulations, providing the formulations achieve administration of a nicotinic compound as described herein. See *Remington's Pharmaceutical Sciences* ($18^{th}$ ed.; Mack Publishing Company, Eaton, Pa., 1990), which is incorporated herein by reference in its entirety.

For example, solid dosage forms may be formulated so as to provide a delayed release of the active agent (i.e., the nicotinic compound), such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Solid dosage forms according to the present invention may also be sustained release (i.e., releasing the active agent over a prolonged period of time), and may or may not also be delayed release. Sustained release formulations are known in the art and are generally prepared by dispersing an active agent within a matrix of a gradually degradable or hydrolyzable material, such as an insoluble plastic, a hydrophilic polymer, or a fatty compound. Alternatively, a solid dosage form may be coated with such a material.

Compositions can be co-extruded, laminated or formed so as to have sandwich-type forms; and hence the location of nicotine and other ingredients can be controlled in order to provide the desired features such as performance, behavior, interaction or non-interaction with other ingredients, storage stability, and the like. In addition, mixtures of component ingredients can be formulated and manufactured into core/shell types of configurations (e.g., lozenge types of products that have an inner region and at least one additional overlayer), with the various regions of such products having differing overall compositions or properties. Thus, for example, the nicotinic compound can have a relatively high concentration towards the inner region of the product, or a relatively high concentration towards the outer region of the product.

One particularly preferred type of a representative composition incorporating nicotine as an active ingredient, and that comprises nicotine in an orally provided form, has the form of a lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference.

The amount of the composition of the invention contained within each piece or unit of lozenge type of product can vary. For example, a representative unit for lozenge products generally weighs at least about 100 mg, often at least about 200 mg, and frequently at least about 300 mg; while the weight of a representative unit for such products generally does not exceed about 1.5 g, often does not exceed about 1 g, and frequently does not exceed about 0.75 g.

The amount of active ingredient within the overall composition can vary. For a composition intended for oral consumption by insertion into the mouth of the subject (e.g., a lozenge or the like), the amount of nicotine within each dosage piece or unit typically is at least about 0.5 mg, generally is at least 1 mg, often is at least about 1.5 mg, and frequently is at least about 2 mg; while the amount of nicotine within each piece typically does not exceed about 10 mg, generally does not exceed about 8 mg, often does not exceed about 6 mg, and frequently does not exceed about 5 mg, calculated as nicotine base. Exemplary types of such products can incorporate about 2 mg, about 2.5 mg, about 3 mg, about 3.5 mg and about 4 mg of nicotine per piece or unit, calculated as nicotine base.

Compositions of the present invention incorporate a pharmaceutically effective amount of nicotine. The dose of active ingredient (i.e., all the various nicotine forms) is preferably that amount effective to treat some symptoms of, or prevent occurrence of the symptoms of, the condition, disease, or disorder from which the subject or patient suffers. By "effective amount", "therapeutic amount" or "effective dose" is meant that amount sufficient to elicit the desired pharmacological or therapeutic effects, thus resulting in effective prevention or treatment of the condition, disease, or disorder. Thus, an effective amount of active ingredient is an amount sufficient to enter relevant regions of the body (e.g., to pass across the blood-brain barrier of the subject), to bind to relevant receptor sites in the CNS and PNS of the subject, and/or to elicit neuropharmacological effects (e.g., elicit neurotransmitter secretion, thus resulting in effective prevention or treatment of the condition, disease, or disorder). Prevention of the disorder is manifested, for example, by delaying the onset of the symptoms of the condition, disease, or disorder. Treatment of the disorder is manifested by, for example, a decrease in the symptoms associated with the condition, disease, or disorder or an amelioration of the reoccurrence of the symptoms thereof.

For compositions of the present invention, the intended daily dose of the active ingredient can vary. The overall dose of active ingredient can depend upon factors such as the weight of the subject ingesting the composition, the condition being treated, the state or severity of the disease or disorder being treated, the desired pharmacological effect, or other such factors. Typically, the amount of nicotine active ingredient, calculated as nicotine base, administered to a subject per day is at least about 2 mg, often is at least about 4 mg, and frequently is at least about 10 mg. Typically, the amount of nicotine active ingredient administered to a subject per day does not exceed about 60 mg, often does not exceed about 50 mg, and frequently does not exceed about 40 mg. See also, for example, the types of dosing regimens and administration techniques set forth in U.S. Pat. No. 5,593,684 to Baker et al.; U.S. Pat. No. 6,660,754 to Kyle et al.; and US Pat. Pub. Nos. 2004/0006113 to Sachs; 2005/0214229 to Pinney et al.; 2008/0124283 to Andersen; and 2009/0293895 to Axelsson et al.; which are incorporated herein by reference.

Representative compositions incorporating nicotine as an active ingredient can have various types of formats and configurations, and as a result, the character, nature, behavior, consistency, shape, form, size and weight of the composition can vary. The shape of a representative composition can be generally spherical, cylindrical (e.g., ranging form the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, caplet, pouch and gum types of products that traditionally have been employed for the administration of pharmaceutical types of products. The general nature of a representative composition can be soft or hard to the feel, or of intermediate softness or hardness; and as such, the composition can be considered to be malleable, flexible, chewy, resilient, brittle, or the like. When administered orally, various components of the product can be considered to be readily dispersible or slow to disperse, or those various components can dissolve at varying rates (e.g., from relatively fast to relatively slow). As a result, for compositions ingested by insertion in the mouth of the human subject, the release rate of active ingredient during use of the product can vary from relatively fast to relatively slow, depending upon factors such as the design of the product and the use of product by the subject using that product. See also, by way of example, the types of products proposed in U.S. Pat. No. 4,655,231 to Ray et al.; U.S. Pat. No. 5,147,654 to Place et al.; U.S. Pat. No. 5,543,424 to Carlsson et al.; U.S. Pat. No. 6,268,386 to Thompson; U.S. Pat. No. 6,319,510 to Yates; U.S. Pat. No. 6,488,953 Halliday et al.; U.S. Pat. No. 6,709,671 to Zerbe et al.; U.S. Pat. No. 7,025,983 to Leung et al.; U.S. Pat. No. 7,105,173 to Rolling; U.S. Pat. No. 7,115,297 to Stillman; U.S. Pat. No. 7,435,749 to Knight; and U.S. Pat. No. 7,491,406 to Leung et al.; and US Pat. Pub. Nos. 2006/0198873 to Chan et al.; 2006/0240087 to Houze et al.; 2006/0204559 to Bess et al.; 2007/0269492 to Steen et al.; 2008/0020050 to Chau et al.; 2008/0286340 to Andersson et al.; 2008/0292683 to Sanghvi et al.; and 2009/0004248 to Bunick et al.; which are incorporated herein by reference.

In certain embodiments, the nicotine-containing pharmaceutical composition is transparent or translucent as defined herein. Transparency/translucency can be determined by any means commonly used in the art; however, it is commonly measured by spectrophotometric light transmission over a range of wavelengths (e.g., from about 400-700 nm). Transmission measurements for the nicotine-containing products of the present invention are typically comparable to or higher than those of traditional nicotine-containing products. Translucency can also be confirmed by visual inspection by simply holding the product up to a light source and determining if light travels through the product in a diffuse manner.

The manners and methods used to formulate and manufacture the nicotine-containing composition can vary. Typical conditions associated with manufacture of pharmaceutical types of products include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, atmospheric control (e.g., nitrogen atmosphere), airflow experienced by the various ingredients during the manufacturing process, and other similar types of factors. Additionally, various process steps involved in product manufacture can involve selection of certain solvents and processing aids, use of heat and radiation, refrigeration and cryogenic conditions, ingredient mixing rates, and the like. The manufacturing conditions also can be controlled due to selection of the form of various ingredients (e.g., solid, liquid, or gas), particle size or crystalline nature of ingredients of solid form, concentration of ingredients in liquid form, or the like. Ingredients can be processed into the desired composition by techniques such as extrusion, compression, spraying, and the like.

For example, the compositions can be prepared via any method commonly used for the preparation of hard boiled confections. Exemplary methods for the preparation of hard confections can be found, for example, in LFRA Ingredients Handbook, Sweeteners, Janet M. Dalzell, Ed., Leatherhead Food RA (December 1996), pp. 21-44, which is incorporated herein by reference.

Typically, the products of the invention are prepared by first preparing a first mixture of ingredients. The composition of the first mixture of ingredients can vary; however, it typically comprises a sugar substitute and may contain various optional additional substances (e.g., the sugar alcohol syrup, NaCl, preservatives, further sweeteners, water, and/or flavorings). In certain embodiments, the first mixture of ingredients comprises the sugar substitute and sugar alcohol syrup (e.g., maltitol syrup or xylitol syrup). Typically, the first mixture of ingredients does not contain the nicotinic compound.

The first mixture of ingredients is heated until it melts; subsequently, the mixture is heated to or past the hard crack stage. In confectionary making, the hard crack stage is defined as the temperature at which threads of the heated mixture (obtained by pulling a sample of cooled syrup between the thumb and forefinger) are brittle or as the temperature at which trying to mold the syrup results in cracking. According to the present method, the temperature at which the hard crack stage is achieved can vary, depending on the specific makeup of the product mixture but generally is between about 145° C. and about 170° C. (e.g., about 165° C.), Typically, the mixture is not heated above about 171° C., which is the temperature at which caramelization begins to occur. In the processes of the present invention, the mixture is typically heated to the hard crack stage temperature or above and then allowed to cool. The heating can be conducted at atmospheric pressure or under vacuum. Typically, the method of the present invention is conducted at atmospheric pressure.

In one exemplary embodiment, the first mixture of ingredients comprises a high percentage of isomalt and the mixture is heated past the hard crack stage (e.g., to about 165° C.). The mixture is heated to this temperature and then removed from the heat to allow the mixture to cool. At one or more predetermined temperatures, certain additional components are added. For example, in certain embodiments, various components are added when the melt has cooled to about 143° C. For example, certain components that may be added at this point include, but are not limited to, buffers, water, and/or the nicotinic compound. In some embodiments, various components are added when the melt has cooled to about 120° C. For example, certain components that may be added at this point include, but are not limited to, flavorants, the nicotinic compound, water, and/or sweeteners. Certain flavorants are volatile and are thus preferably added after the mixture has cooled somewhat. Further, in some embodiments, it is desirable to add the tobacco component at a somewhat cooled temperature. As noted above, in certain embodiments, various components are added at different stages in the cooling process. However, it is also possible to combine these components and add them together at a single stage in the cooling process.

The combined mixture is then formed into the desired shape. In certain embodiments, the mixture is poured directly into molds, formed (e.g., rolled or pressed) into the desired shape, or extruded. If desired, the mixture can be extruded or injection molded. In certain embodiments, the mixture is formed or extruded into a mold of desired shape in an enclosed system, which may require decreased temperature and which may limit evaporation of certain mixture components. For example, such a system may limit the evaporation of volatile components including, but not limited to, the nicotinic compound and/or flavorants. Other methods of producing nicotine-containing products such as lozenges are also intended to be encompassed herein. In use, the compositions of the present invention are typically administered in a form adapted for buccal or sublingual delivery. In certain embodiments, the compositions are in a form suitable for oral ingestion. For example, nicotine-containing compositions can be administered and employed using the manners and methods typically used for the administration of traditional types of nicotine-containing lozenges.

The compositions of the present invention can be used for treatment of a wide variety of conditions, diseases, and disorders responsive to stimulation of one or more types of nicotinic acetylcholinergic receptors (nAChRs). The compositions can be used to treat those types of conditions, diseases, and disorders that have been reported to be treatable through the use or administration of nicotine as an agonist of nAChRs. As such, the compositions can be used to treat various CNS conditions, diseases, and disorders, and the compositions also can be used as smoking cessation aids (i.e., as components of NRT). Exemplary conditions, diseases or disorders that can be treated include cognitive disorders such as Alzheimer's disease and attention deficit disorder, schizophrenia, Parkinson's disease, Tourette's syndrome, ulcerative colitis, dry eye disease, hypertension, obesity, and hemorrhoids. Compositions of the invention may also find use as a treatment to reduce stress or pain.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Aspects of the present invention are more fully illustrated by the following examples, which are set forth to illustrate certain aspects of the present invention and are not construed as limiting thereof.

EXPERIMENTAL

The following examples are provided in order to further illustrate the invention but should not be construed as limiting the scope thereof. Unless otherwise noted, all parts and percentages are by weight.

Hard-boiled lozenges are prepared according to the following process. Isomalt and maltitol syrup (or xylitol syrup) are heated to melting without stirring, to hard crack temperature (e.g., 165° C.). The melt is cooled to approximately 143° C., with very slight, discontinuous stirring. Other components (e.g., buffer, nicotine, sweetener, and/or flavorants) are added to the mixture and folded in carefully with a spatula without introducing much air into the melt. The melt is further cooled to about 120° C. Further components (e.g., buffer, nicotine, sweetener, and/or flavorants) are added to the mixture and folded in carefully with a spatula without introducing much air into the melt. The final mixture is poured into a glass beaker, the contents are poured from the beaker in a chord on a metal brick, in breakaway molds with niches of suitable dimensions, or in molds (for individual lozenges). It may be necessary to reheat the beaker in order to obtain a viscosity of the melt so it flows easily. The melt is cooled for a time suitable for solidifying (e.g., at room temperature).

Table 1 below provides six examples of product compositions prepared according to the invention as outlined above.

TABLE 1

Formulations of Samples 1-6

| Component | Sample 1 (g) | Sample 2 (g) | Sample 3 (g) | Sample 4 (g) | Sample 5 (g) | Sample 6 (g) |
|---|---|---|---|---|---|---|
| Isomalt | 279.6 | 279.6 | 278.8 | 279.6 | 281.85 | 278.85 |
| Maltitol syrup | 15.0 | 15.0 | 15.0 | — | 15.0 | — |
| Sodium carbonate | 2.25 | 2.25 | 2.25 | 2.25 | — | 2.25 |
| Acesulfame K | 0.15 | 0.15 | 0.15 | 0.15 | 0.15 | 0.15 |
| Mint-derived Flavorant | 0.75 | 0.75 | 0.75 | 0.75 | 0.75 | 1.5 |
| Peppermint Flavorant | 0.75 | 0.75 | — | — | — | 0.75 |
| Mint Flavorant | — | — | 1.5 | 0.75 | 0.75 | — |
| Water | 7.75 + 10* | 4 | — | 4 | 4 | 4 |
| Nicotine bitartrate dihydrate | 1.5 | 1.5 | 1.5 | 1.5 | 1.5 | 1.5 |
| Xylitol syrup | — | — | — | 15.0 | — | 15.0 |

*Added in two separate process steps as provided in Table 2, below (7.75 g added in Addition 1, 10 g added in Addition 2)

In Table 2 below, each of the six samples is described in terms of process steps used to produce the product. The steps including the step of forming a first mixture (e.g., Isomalt and maltitol syrup), melting the first mixture at a temperature above the hard crack stage, cooling the first mixture to about 143° C. and then adding a second composition to the first mixture (i.e., Addition 1 in the table), and finally cooling the product mixture to 120° C. before adding the final ingredients (i.e., Addition 2 in the table).

TABLE 2

Preparation of Samples 1-6

| Process step | Sample 1 | Sample 2 | Sample 3 | Sample 4 | Sample 5 | Sample 6 |
|---|---|---|---|---|---|---|
| Melt | Isomalt, maltitol syrup | Isomalt, maltitol syrup, sodium carbonate | Isomalt, maltitol syrup, sodium carbonate | Isomalt, xylitol syrup, sodium carbonate | Isomalt, maltitol syrup | Isomalt, xylitol syrup, sodium carbonate |
| Cooling to 143° C. | yes | yes | yes | yes | yes | yes |
| Addition 1 | Sodium carbonate, water | — | Nicotine bitartrate dihydrate | Nicotine bitartrate dihydrate, water | Nicotine bitartrate dihydrate, water | Nicotine bitartrate dihydrate, water |
| Cooling to 120° C. | yes | yes | yes | yes | yes | yes |
| Addition 2 | Nicotine bitartrate dihydrate, water, acesulfame K, Cooling Flavorant, Peppermint Flavorant | Nicotine bitartrate dihydrate, water, acesulfame K, Cooling Flavorant, Peppermint Flavorant | Acesulfame K, Cooling Flavorant, Mint Flavorant | Acesulfame K, Cooling Flavorant, Mint Flavorant | Acesulfame K, Cooling Flavorant, Mint Flavorant | Acesulfame K, Cooling Flavorant, Peppermint Flavorant |
| Appearance (translucent unless otherwise described) | Brown | Brown | Brown, opaque | Brown | Slightly yellow | Brown |

What is claimed is:

1. A method of preparing a nicotine-containing pharmaceutical composition, comprising:
    (i) mixing a non-hygroscopic sugar substitute capable of forming a glassy matrix in an amount of at least about 80% by weight and a sugar alcohol syrup in a melted state to form a mixture;
    (ii) cooling the mixture to about 143° C. and incorporating a nicotinic compound into the cooled mixture; and
    (iii) further cooling the mixture to room temperature to form a solid nicotine-containing pharmaceutical composition,
    wherein the mixture does not comprise a gum component,
    wherein the solid nicotine-containing pharmaceutical composition is translucent, and
    wherein the incorporating step further comprises incorporating one or more buffering agents into the cooled mixture, wherein the one or more buffering agents are selected from the group consisting of arginine, asparagine, glutamic acid, glutamine, glycine, histidine, isoleucine, leucine, lysine, methionine, phenylalanine, serine, threonine, valine, cysteic acid, N-glycylglycine, ornithine, and combinations thereof.

2. The method of claim 1, wherein at least a portion of the nicotinic compound is in the form of a free base, a salt, a complex, or a solvate.

3. The method of claim 1, wherein the nicotinic compound is nicotine polacrilex.

4. The method of claim 1, wherein the nicotinic compound is sorbed onto a porous particulate carrier.

5. The method of claim 4, wherein the porous particulate carrier comprises microcrystalline cellulose.

6. The method of claim 1, wherein the sugar substitute is isomalt.

7. The method of claim 1, wherein the sugar alcohol syrup is in an amount sufficient to slow recrystallization of the sugar substitute in melted form.

8. The method of claim 1, wherein the sugar alcohol syrup is maltitol syrup or xylitol syrup.

9. The method of claim 1, wherein the pharmaceutical composition comprises at least about 85% by weight of the sugar substitute.

10. The method of claim 1, wherein the pharmaceutical composition comprises at least about 4.0% by weight of sugar alcohol syrup.

11. The method of claim 1, wherein the pharmaceutical composition comprises at least about 4.5% by weight of sugar alcohol syrup.

12. The method of claim 1, wherein the composition is in the form of a lozenge or tablet.

13. The method of claim 1, further comprising adding one or more components selected from the group consisting of flavorants, sweeteners, and NaCl at a temperature of about 143° C. along with the nicotinic compound added in step or at a second temperature below about 143° C. after step ii.

14. The method of claim 13, wherein the amount of flavorant is from about 0.1 to about 0.5 percent by weight of the pharmaceutical composition.

15. The method of claim 13, wherein the flavorant is vanillin or mint flavor.

16. The method of claim 13, wherein the sweetener comprises sucralose.

17. The method of claim 13, wherein the amount of NaCl is from about 0.5 to about 1 percent by weight of the pharmaceutical composition.

18. The method of claim 1, wherein the mixing step comprises heating the sugar substitute and the sugar alcohol syrup to a temperature above the hard crack stage of the sugar substitute and wherein the about 143° C. of the incorporating step is below the hard crack stage of the sugar substitute.

19. The method of claim 18, wherein the hard crack stage is about 145° C. to about 155° C. and the sugar substitute and the sugar alcohol syrup are heated at a temperature between the hard crack stage and about 171° C.

20. A method of preparing a nicotine-containing pharmaceutical composition, comprising:
(i) mixing a first non-hygroscopic sugar alcohol capable of forming a glassy matrix in an amount of at least about 80% by weight and a second sugar alcohol in an amount of at least about 4.5% by weight and up to about 20% by weight in a melted state to form a mixture, wherein the mixture does not comprise a gum component;
(ii) cooling the mixture to about 143° C. and incorporating a nicotinic compound into the cooled mixture, wherein the incorporating step further comprises incorporating one or more buffering agents into the cooled mixture, wherein the one or more buffering agents are selected from the group consisting of arginine, asparagine, glutamic acid, glutamine, glycine, histidine, isoleucine, leucine, lysine, methionine, phenylalanine, serine, threonine, valine, cysteic acid, N-glycylglycine, ornithine, and combinations thereof; and
(iii) further cooling the mixture to room temperature to form a solid nicotine-containing pharmaceutical composition, wherein the solid nicotine-containing pharmaceutical composition is translucent.

21. The method of claim 20, wherein both the non-hygroscopic sugar alcohol and the second sugar alcohol are selected from the group consisting of erythritol, threitol, arabitol, xylitol, ribotol, mannitol, sorbitol, dulcitol, iditol, isomalt, maltitol, lactitol, polglycitol, and mixtures thereof.

22. The method of claim 20, wherein the first non-hygroscopic sugar alcohol is isomalt and the second sugar alcohol is maltitol.

23. The method of claim 20, wherein at least a portion of the nicotinic compound is in the form of a nicotine salt of tartrate.

24. The method of claim 20, wherein the composition is in the form of a lozenge or tablet.

* * * * *